(12) United States Patent
Huber et al.

(10) Patent No.: US 7,985,597 B2
(45) Date of Patent: *Jul. 26, 2011

(54) PROCESS AND APPARATUS FOR PROVIDING A GASEOUS SUBSTANCE FOR THE ANALYSIS OF CHEMICAL ELEMENTS OR COMPOUNDS

(75) Inventors: Christof Huber, Bern (CH); Markus Leuenberger, Kaufdorf (CH)

(73) Assignee: Universitat Bern, Bern (CH)

( * ) Notice: Subject to any disclaimer, the term of this patent is extended or adjusted under 35 U.S.C. 154(b) by 726 days.

This patent is subject to a terminal disclaimer.

(21) Appl. No.: 10/417,720

(22) Filed: Apr. 16, 2003

(65) Prior Publication Data

US 2003/0228708 A1 Dec. 11, 2003

(30) Foreign Application Priority Data

Apr. 16, 2002 (DE) .................................. 102 16 974
Nov. 30, 2002 (DE) .................................. 102 56 009

(51) Int. Cl.
*G01N 7/00* (2006.01)
*G01N 1/00* (2006.01)
*G01N 30/02* (2006.01)
*H01J 49/00* (2006.01)

(52) U.S. Cl. ...... 436/181; 73/23.37; 73/23.41; 250/288; 436/161

(58) Field of Classification Search .................. 436/146, 436/52, 136–138, 174–181
See application file for complete search history.

(56) References Cited

U.S. PATENT DOCUMENTS

| 4,046,510 A | 9/1977 | Becker et al. |
| 4,063,891 A | 12/1977 | Becker et al. |
| 4,066,404 A | 1/1978 | Morgan et al. |
| 4,277,438 A | 7/1981 | Ejzak |
| 4,740,473 A | 4/1988 | Tomlin |
| 4,886,528 A | 12/1989 | Aaltonen et al. |
| 5,012,052 A | 4/1991 | Hayes |
| 5,102,805 A | 4/1992 | Baughman et al. |
| 5,308,979 A | 5/1994 | Villa-Aleman |
| 5,314,827 A | 5/1994 | Schmidt et al. |
| 5,643,799 A | 7/1997 | Atwater et al. |
| 5,661,038 A | 8/1997 | Brenna et al. |
| 5,672,516 A | 9/1997 | Jeffers |
| 5,766,954 A * | 6/1998 | Freedman et al. ............ 436/144 |

(Continued)

FOREIGN PATENT DOCUMENTS

CH         442 806         8/1965

(Continued)

OTHER PUBLICATIONS

WPI, Accession No. 1994, 103999 & JP 060050956 A (Shimadzu).
W.A. Brand, H. Avak, R. Seeforf, D. Hofmann, TH. Conradi, "New Methods for Fully Automated Isotope Ratio Determination From Hydrogen at the Natural Abundance Level", Isotopes Environ. Health Stud., 1996, vol. 32, pp. 263-273, (1996).

(Continued)

*Primary Examiner* — Krishnan S Menon
*Assistant Examiner* — Dirk Bass
(74) *Attorney, Agent, or Firm* — Laurence P. Colton; Smith Risley Tempel Santos LLC (57) ABSTRACT

The invention relates to a process and to an apparatus for providing a gaseous substance for the analysis of chemical elements or compounds. In one embodiment, a starting substance is continuously admixed with a reagent substance. This results in a gaseous reaction product which contains information about the elements of the starting substance, and a residual substance. The gaseous reaction product is separated from the residual substance and removed for analysis. One application is the isotopic analysis of oxygen or hydrogen from water.

39 Claims, 6 Drawing Sheets

U.S. PATENT DOCUMENTS

| | | | |
|---|---|---|---|
| 5,869,344 A * | 2/1999 | Linforth et al. | 436/173 |
| 5,932,791 A * | 8/1999 | Hambitzer et al. | 73/19.01 |
| 5,942,439 A | 8/1999 | Holt et al. | |
| 5,979,228 A | 11/1999 | Smith et al. | |
| 6,319,723 B1 * | 11/2001 | Jeffers et al. | 436/133 |
| 7,213,443 B2 * | 5/2007 | Hilkert et al. | 73/23.37 |
| 2002/0068017 A1 * | 6/2002 | Naatz et al. | 422/80 |

FOREIGN PATENT DOCUMENTS

| | | |
|---|---|---|
| DE | 199 38 395 A1 | 2/1988 |
| DE | 40 12 454 C 1 | 8/1991 |
| DE | 9314169 U1 | 2/1994 |
| DE | 43 32 127 C2 | 4/1994 |
| DE | 43 33 208 A1 | 6/1994 |
| DE | 690 16 900 T 2 | 2/1995 |
| DE | 43 33 208 C 2 | 4/1995 |
| DE | 44 13 197 A1 | 10/1995 |
| DE | 43 32 127 C 2 | 1/1998 |
| DE | 196 50 444 A1 | 6/1998 |
| DE | 199 38 395 A 1 | 2/2001 |
| DE | 199 56 632 C 1 | 6/2001 |
| DE | 102 16 974.8 | 1/2003 |
| EP | 0 256 684 A2 | 2/1988 |
| EP | 0 306 332 B1 | 3/1989 |
| EP | 0 507 287 A2 | 10/1992 |
| EP | 0 507 287 B1 | 10/1992 |
| EP | 0 509 316 B1 | 10/1992 |
| EP | 0 565 248 A2 | 10/1993 |
| EP | 0 729 577 B1 | 9/1996 |
| EP | 0 729 577 B1 | 3/2001 |
| GB | 2309782 A | 6/1997 |
| JP | 58028662 | 2/1983 |
| JP | 59141782 | 1/1986 |
| JP | 63090175 | 10/1989 |
| VG | 0 306 332 A2 | 3/1989 |
| WO | WO 97/31257 | 8/1997 |

OTHER PUBLICATIONS

Tyler B. Coplen, Joe D. Wildman, Julie Chen, "Improvements in the Gaseous Hydrogen-Water Equilibration Technique for Hydrogen Isotope Ratio Analysis", Analytical Chemistry, vol. 63, No. 9, May 1, 1991, pp. 911-912.

S. Epstein, T. Mayeda, "Variation of $O^{18}$ Content of Waters from Natural Sources", Geochimica et Cosmochimica Acta, 1953, vol. 4, pp. 213-224.

Juske Horita, "Hydrogen Isotope Analysis of Natural Waters Using An H2-Water Equilibration Method: A Special Implication to Brines", Chemical Geology (Isotope Science Section), 72 (1988), pp. 89-94.

Finnigan MAT GmbH, "GasBench II: $^{18}$O-Equilibration on Water, Fruit Juice, and Wine", Finnigan MAT Application Flash Report No. G 30, 4 pages.

C. Huber, M: Leuenberger, "Fast high-precision on-line determination of hydrogen isotope ratios of water or ice by continuous-flow isotope ratio mass spectrometry", Rapid Commun. Mass Spectrom. 2003; 17, pp. 1319-1325.

C. Huber, M. Leuenberger, Oliver Zumbrunnen, "Continuous Extraction of Trapped Air from Bubble Ice or Water for On-Line Determination of Isotope Ratios", American Chemical Society, pp. A-1, (2003).

M. Leuenberger, C. Huber, "On-Line Determination of Oxygen Isotope Ratios of Water or Ice by Mass Spectrometry", Analytical Chemistry, vol. 74, No. 18, pp. 4611-4617, (2002).

Andreas Sigg, Katrin Fuhrer, Martin Anklin, Thomas Staffelbach, Daniel Zurmuhle, "A Continuous Analysis Technique for Trace Species in Ice Cores", Environ. Sci, Technol., vol. 28, No. 2, 1994, pp. 204-208.

* cited by examiner

Fig. 6 (in particular for Example 1, Table 2 and Example 3, Table1)

Fig. 7 (in particular for Example 5, Table 2 and Example 6, Table1)

US 7,985,597 B2

PROCESS AND APPARATUS FOR PROVIDING A GASEOUS SUBSTANCE FOR THE ANALYSIS OF CHEMICAL ELEMENTS OR COMPOUNDS

RELATED APPLICATIONS

This application claims priority to German Patent Applications Serial Number 102 16 974.8 and Serial Number 102 56 009.9, filed on Apr. 16, 2002 and Nov. 30, 2002, respectively, the disclosures of which are hereby incorporated by reference in their entireties.

FIELD OF THE INVENTION

The present invention relates generally to the field of chemical analysis. More specifically, the invention relates to a process and to an apparatus for providing a gaseous substance for the analysis of chemicals elements and/or compounds

BACKGROUND OF THE INVENTION

The mass spectrometry determination of elemental and of isotopic information are important analytical methods. The use of a mass spectrometer makes it possible to identify individual chemical elements or compounds. A significant application in this context is the determination of the isotopic ratios of individual elements in a starting substance, for example $^{18}O/^{16}O$ in water or the determination of different hydrogen isotopes. Since the variations of the isotopic ratios are minimal, extremely precise measurement apparatus and processes are required for the analysis. Therefore, importance attaches not only to the mass spectrometry itself, but also to the preparation of the chemical elements or compounds for the analysis to be carried out.

In an existing isotope analysis process, the oxygen of water is not analyzed directly. Rather, the isotopic information is transferred to carbon dioxide ($CO_2$) by the method of equilibration. To this end, a small amount of the water to be analyzed is introduced into a vessel, as is an even smaller amount of $CO_2$. The proportion of water is higher by a factor of about $10^3$ than the proportion of $CO_2$. The vessel is shaken and there is mixing of the isotopic information from the oxygen of the water and the $CO_2$. Owing to the significantly greater proportion of water, the original isotopic information from the $CO_2$ is virtually suppressed. The equilibrated $CO_2$ then contains the isotopic information of the oxygen from the water and is removed directly or using a carrier gas and fed to an isotope mass spectrometer for analysis. The disadvantage of this system is the necessary provision of the vessels for equilibrating water and $CO_2$, and also the residence time in the vessels required therefor. This is disadvantageous, especially in the context of relatively large sample sizes.

In this process, the $CO_2$ added to the water has the function of a reagent substance. After the equilibration, the gaseous $CO_2$ may be referred to as a reaction product, and the water as a residual substance. The reaction product is required for the analysis.

Further processes are conceivable in which a starting substance is not directly analyzed, but rather information is passed on therefrom to a gaseous reaction product. It is important that there is a means for rapid and reliable, precise implementation.

Accordingly, it is desirable to provide a process and an apparatus which allows chemical elements or compounds to be rapidly and precisely prepared for analysis.

SUMMARY OF THE INVENTION

It is one object of the present invention to provide a process and apparatus for the production of gaseous substances for the analysis of chemical elements or compounds.

One embodiment of the present invention provides a process for providing a gaseous substance for the analysis of chemical elements or compounds. In this process, the elements or compounds are contained in a starting substance. The starting substance is continuously admixed with a reagent substance. At least one gaseous reaction product and a residual substance are formed. The gaseous reaction product contains information about the elements or compounds of the starting substance. The gaseous reaction product is separated from said residual substance; and the reaction product is removed for an analysis.

In another embodiment of the present invention, an apparatus is provided for providing a gaseous substance for the analysis of chemical elements or compounds. This apparatus comprises a reaction unit for the reaction of a starting substance containing the chemical elements or compounds with a reagent substance. The apparatus also comprises a means for continuously feeding the starting substance and the reagent substance into the reaction unit as well as a separating unit that comprises means for separating a gaseous reaction product from a residual substance. The separating unit has a first outlet from for the residual substance and a second outlet for the reaction product. A means for passing the reaction product on from the separating unit to an analytical instrument is also provided.

BRIEF DESCRIPTION OF THE DRAWINGS

Other objects and advantages of the present invention will become apparent upon reading the detailed description of the invention and the appended claims provided below, and upon reference to the drawings, in which:

FIGS. 5a to 5d show details of an equilibration unit for hydrogen, wherein

DETAILED DESCRIPTION OF THE INVENTION

The present invention is directed generally to system and method for providing a gaseous substance for analysis of chemical elements and/or compounds. In one embodiment, a process according to the invention includes the following features:

a) the elements or compounds are contained in a starting substance,
b) the starting substance is continuously admixed with a reagent substance,
c) at least one gaseous reaction product is formed which contains information about the elements or compounds of the starting substance, and a residual substance,
d) the reaction product is separated from the residual substance,
e) the reaction product is finally removed for an analysis.

One of the essential features of the novel process compared to the example illustrated at the outset is the continuous combination of the starting substance with the reagent substance. The gaseous reaction product is also formed continuously. Finally the separation of the reaction product from the residual substance likewise takes place continuously. The entire process is therefore continuous and can be carried out without breaks dictated by separate steps.

A preferred field of application is the isotopic or elemental analysis, and also the quantitative determination of elements or compounds in a starting substance. The information contained in the reaction products may therefore also be the elements or compounds themselves. For the sake of simplicity, unless otherwise stated, isotopic information and information on compounds is also referred to as elemental information.

As explained above, the reaction results in the reaction product and the residual substance. Further substances may be formed in addition which are removed. For later analysis, interest attaches to the gaseous reaction product which contains the information about the elements or compounds of the starting substance.

For the provision of oxygen on the one hand and hydrogen on the other hand, processes which differ in their detail may be used. For instance, for the provision of oxygen from water, the latter (in particular liquid water) and a suitable gas are equilibrated. The gas used is preferably $CO_2$. The application of the inventive idea to the example mentioned at the outset of an isotopic analysis of the elements contained in water results in the following steps:
a) oxygen and hydrogen are constituents of the water,
b) the water is continuously admixed with $CO_2$ or $H_2$ as the reagent substance,
c) at least gaseous $CO_2$ or $H_2$ are formed continuously as the reaction product and contain the isotopic information of hydrogen or oxygen of the starting substance, and water or steam are formed as the residual substance,
d) $CO_2$ or $H_2$ are separated from the residual substance,
e) $CO_2$ or $H_2$ are finally removed for analysis.

The process according to the invention provides for the first time the continuous equilibration of oxygen and/or hydrogen with a suitable gas. Continuous feeding of water is also possible for the first time.

The continuously fed water may be present in gaseous form as steam or in liquid form as a mixture of both phases. The separation of water and equilibration gas is preferably effected continuously, as is the feed of the equilibration gas to the isotopic analysis.

Advantageously, at least one of the elements H, O, C, S, P or N is present in the starting substance. The process according to the invention is preferably used for the preparation of the analysis of these elements or corresponding compounds.

For the provision of hydrogen for isotopic analysis, the water may be equilibrated as steam with a suitable gas. Preference is given to using hydrogen as the equilibration gas, though the use of other gases is envisioned within the scope of the present invention. In addition to steam, the water may also contain liquid water.

For the equilibration, preference is given to passing the mixture of water or steam and hydrogen over a catalyst and/or heating it. The catalyst contemplated is in particular platinum.

A carrier gas may be added to the water or hydrogen (or another equilibration gas) during or before the equilibration. The aim is to increase the gas stream after the equilibration by a factor of about $10^2$.

Advantageously, the water (mainly in the form of steam) is separated from residual gases at a steam-permeable membrane. At this stage of the process, the water should be present as steam. The separation is effected using a NAFION tube known per se.

Generally speaking, the residual substance on separation of gaseous reaction product may be liquid, for example water or an aqueous solution. However, another state is also possible, for instance a gaseous residual substance such as steam. The liquid residual substance makes it possible to use special separating processes, for instance at a membrane which is gas-permeable and liquid-impermeable. When separating, it may be advantageous to entrain and remove the gaseous reaction product from a carrier gas stream on a gas side of the membrane. The residual substance then remains on the liquid side of the membrane. The separation is eased by a pressure differential between the water side and the gas side of the membrane. Preference is given to conducting helium as the carrier gas along the gas side. The pressure on the water side, for instance in the mixture of water and $CO_2$, is about half an atmosphere above the pressure on the gas side (e.g. a mixture of carrier gas and $CO_2$).

The starting substance may be a liquid, in particular an aqueous liquid, in which elements or compounds of interest are dissolved, e.g. drinks, in particular wine, mineral water, fruit juice. Useful liquids also include aqueous liquids or solutions such as blood or urine.

When liquid water is used as a starting substance or an aqueous liquid is used, the water may also be provided by continuously melting ice. For instance, it is possible by the process according to the invention to prepare drilled ice cores for an isotopic analysis. When water is continuously provided by constant melting of suitable amounts of ice, the melt water (in liquid form) is continuously aspirated by a pump and passed on for the reaction or equilibration. It is also possible to provide a sample in portions in combination with a continuous further feed. For instance, sample vessels containing liquid water may be connected to a pump. After the sample vessel is emptied, an automatic exchange takes place.

The reagent substance is preferably a gas. In this context, a gas mixture is a gas. However, liquids or solids are also possible.

Materials may be dissolved in the water (starting substance), such as carbonates, sulfates, nitrates, etc.

The invention further contemplates the reaction of at least one constituent of the reagent substance with at least one constituent of the starting substance, resulting in the gaseous reaction product.

As already stated above, the process according to the invention may be utilized in combination with an equilibration. In the equilibration, at least one constituent of the reagent substance equilibrates with at least one of the elements or compounds of the starting substance. This preferably results in isotopic information or other elemental information being transferred or taken up. The information is then present in the reaction product.

In a further alternative of the process according to the invention, the reagent substance changes the pH of the starting substance, which results in the gaseous reaction product being formed. An example of a useful reagent substance is an acid. Some of the reaction product may also already have been present before the reaction. The reaction then increases the proportion of the reaction product in the total amount of reaction product and residual substance.

The invention further contemplates the reaction product and the residual substance being in gaseous form and being separated from one another in this state.

It is also possible to heat at least one of the substances starting substance, reagent substance, reaction product and residual substance. This may effect a better reaction between starting substance and reagent substance or provide a better means of separating reaction product and residual substance. For the provision of oxygen from water, the mixture of water and $CO_2$ is advantageously heated. This accelerates the equilibration or reaction. Temperatures of around 50° C. are desired.

A modification of the process according to the invention relates to applications in which the elements or compounds to be investigated are present as gases or as constituents of gases and are contained in a liquid starting substance in the widest sense (mixture, solution or the like). The starting substance (with the gases) is passed through a degassing unit. The gases are separated there from the liquid starting substance.

In the degassing unit is preferably disposed a membrane which is for separating a gas side from a liquid side and has a reduced pressure on the gas side.

After leaving the degassing unit, the gases are removed for the analysis. The individual steps are carried out continuously. The starting substance is preferably liquid water or at least one aqueous solution in the sense already described above. The elements or compounds present in the starting substance may be, for example, air or its constituents. The process is of particular interest for the isotopic or quantitative analysis, for instance of air constituents in water. The radon content of the dissolved air may also be determined by the analysis which follows.

In one embodiment of the present invention, the apparatus for preparing an analysis of chemical elements or compounds includes
 a) a reaction unit for the reaction of a starting substance containing the elements or compounds with a reagent substance,
 b) a means for continuously feeding the starting substance and the reagent substance into the reaction unit,
 c) in a separating unit are provided means for separating a gaseous reaction product from a residual substance,
 d) the separating unit has a first outlet for the residual substance and a second outlet for the reaction product,
 e) a means for passing the reaction product on from the separating unit to an analytical instrument.

A conceivable reaction unit is a chamber provided with feeds which is otherwise closed, in which the reaction of the starting substance with the reagent substance takes place. The starting substance and the reagent substance are introduced into the reaction unit individually or together, for instance using pumps, or using an elevated pressure or pressure drop provided in another way. Preferred analytical instruments are mass spectrometers, isotope mass spectrometers and elemental analyzers. Other analytical instruments are also possible.

Reaction units and separating units are preferably spatially separated. Means for transferring the reaction product and the residual substance from the reaction unit into the separating unit are then provided.

The separating unit may have a membrane which is gas-permeable and at the same time liquid-impermeable. Alternatively, and taking into account the substances used and the states of matter present, the separating unit may have a membrane which is permeable to steam or certain gases, but impermeable to other gases.

The impermeabilities specified are dependent upon the quality of the particular membrane. In some cases, residues of the substance to be removed succeed in penetrating the membrane with the gases. Additional separating units may be provided to separate the residues mentioned.

In addition, heating equipment may be provided to heat at least one of the substances starting substance, reagent substance, reaction product and residual substance. The heating equipment may also be provided as part of the reaction unit.

In certain cases, the starting substance is present as a solid, for instance as ice. A melt unit for melting the solid starting substance is then advantageously provided. The starting substance is fed from the melt unit to the reaction unit or other units upstream thereof.

With regard to the equipment also, the invention independently contemplates the separation of liquid on the one hand and gas on the other hand. The separation is effected as a preparation for the analysis of chemical elements or compounds.

In an alternative embodiment of the present invention, the apparatus for providing the gaseous substance for the analysis of chemical elements or compounds includes
 a) a degassing unit having a liquid inlet, a liquid outlet and a gas outlet,
 b) in the degassing unit is disposed a gas permeable and liquid impermeable membrane which separates a liquid zone from a gas zone,
 c) the gas zone is coupled to the gas outlet, and the liquid inlet and liquid outlet are coupled to the liquid zone,
 d) from the gas outlet there is a connection to an instrument for the analysis of the elements or compounds.

The instrument contemplated for the analysis is preferably an isotope mass spectrometer (IRMS), an elemental analyzer or another analytical instrument. Downstream of the degassing unit, drying units and/or an open split for the exact metering of the gas may be provided. From there, a controlled fraction of the gas enters an ion source of the IRMS.

Advantageously, the degassing unit has a gas inlet coupled to the gas zone. Carrier gas, in particular helium, flows through the gas inlet into the degassing unit to entrain the gas passing through the membrane.

Exemplary embodiments of the present invention are now described in greater detail with reference to the attached figures and drawings. The foregoing descriptions of these embodiments are intended to be merely illustrative and not limiting of the scope of the invention in any way.

Figure 1:
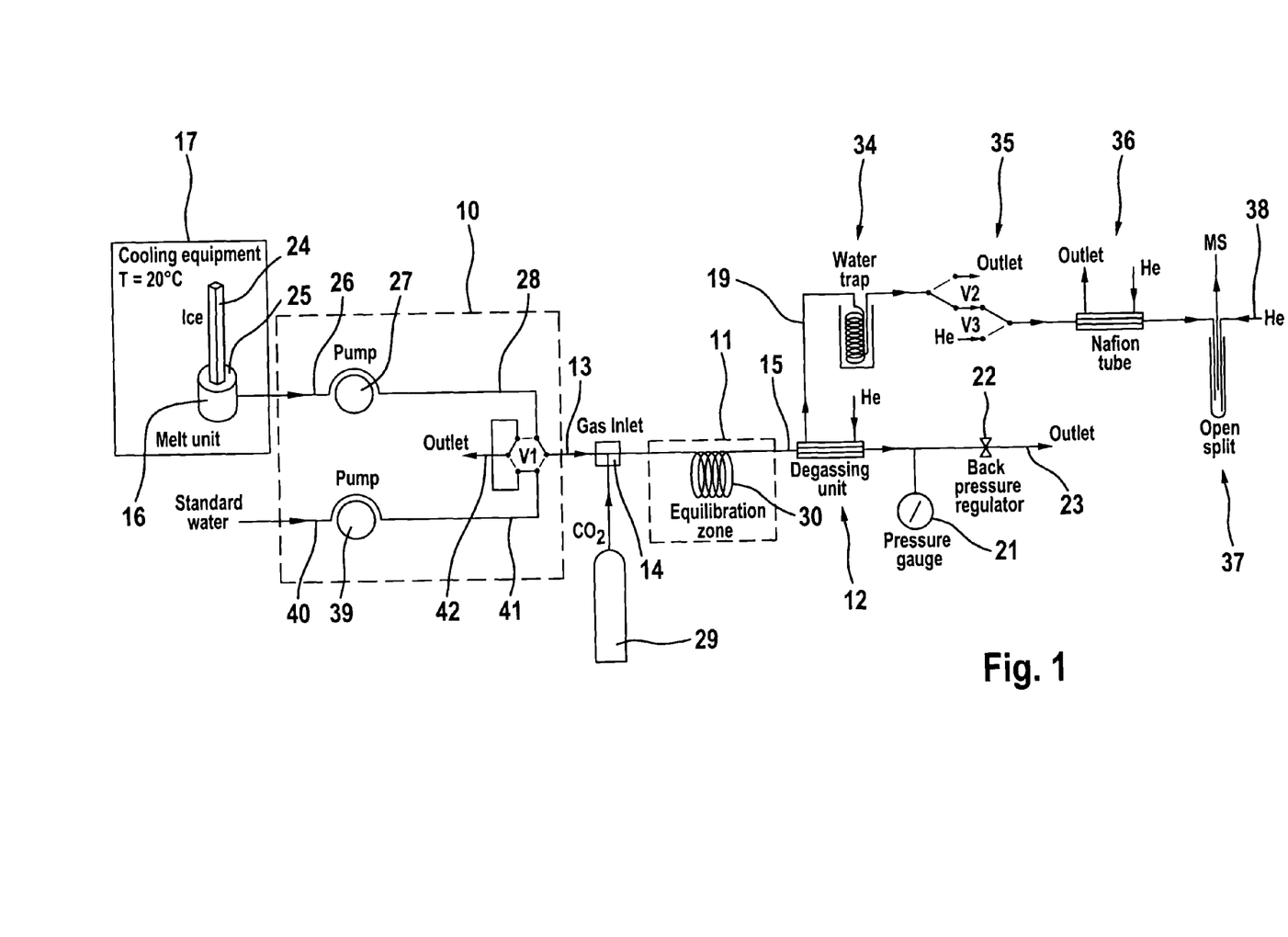
FIG. 1 shows an overview of the individual constituents of the apparatus according to the invention and their combination for the provision of oxygen for isotopic analysis.

An apparatus according to the invention for providing oxygen or hydrogen from water for isotopic analysis includes a water feed unit 10 (dashed), an equilibration unit 11 (dashed) and a degassing unit 12. In a water line 13 between the water feed unit 10 and the equilibration unit 11 is disposed a gas inlet 14. The equilibration unit 11 is connected to the degassing unit 12 via a line 15. Upstream of the water feed unit 10 is disposed a melt unit 16 for melting ice, which is maintained at a constant cold temperature by cooling equipment 17. Alternatively, for example, an upstream X-Y sampling tool (autosampler) may be provided for discrete water samples.

Figure 2:
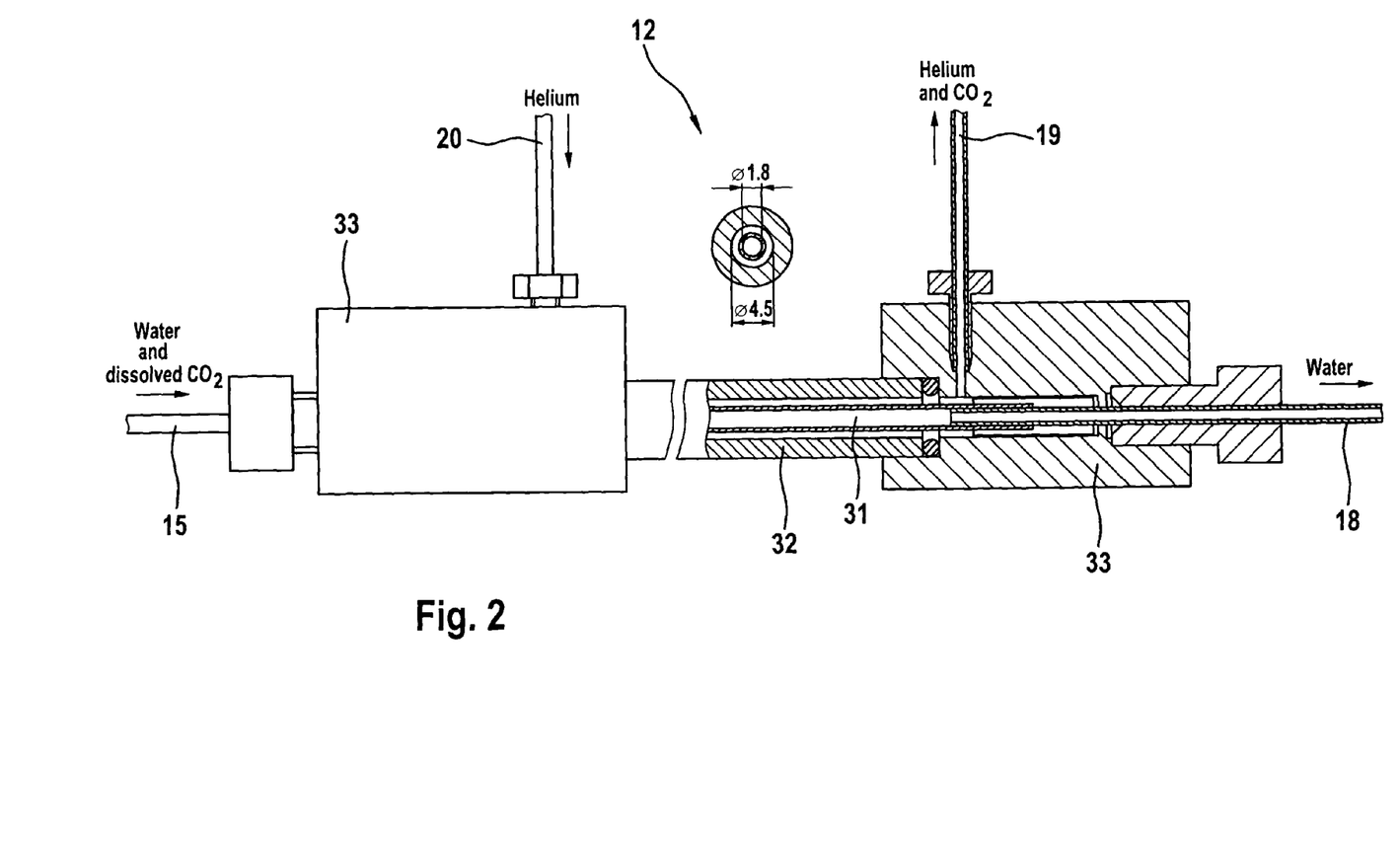
FIG. 2 shows an enlarged illustration of a degassing unit.

The degassing unit 12 has a water outlet 18, a gas outlet 19 and a gas inlet 20. Connected to the water outlet 18 are a pressure gauge 21 and a back pressure regulator 22. Downstream of the back pressure regulator 22 is disposed a waste line 23.

In the cooling equipment 17, an ice rod is provided, for instance from a glaciological drilling, and has a length of 50-100 cm and a cross section of 2×2 cm or the like. One end of the ice rod 24 is melted by the melt unit 16. The liquid water is pumped out via a drillhole (cross section=1 cm$^2$) in the middle of a melt head 25. About 25% of the molten water thus enters an intake line 26 of a very uniformly operating pump 27. This is part of the water feed unit 10 and is in particular a peristaltic pump.

The water passes from the pump 27 via a pressure line 28 and a four-way valve or a six-way valve V1 into the water line 13.

A $CO_2$ reservoir 29 is attached to the gas inlet 14. The $CO_2$ passes through the gas inlet 14 into the water flowing through the water line 13. Specifically, the gas inlet 14 provided is a thin (35 μm), short (15 cm) pressure line (3 bar), from which the $CO_2$ exits and enters the water line 13 in small bubbles. The gas inlet 14 may therefore be referred to as the bubble generator.

Subsequently, the mixture of water and $CO_2$ is conducted through the equilibration unit 11. This has a narrow tube 30 or capillary of length 2 m and diameter 0.75 mm (1/16"). The tube 30 is disposed in a water bath maintained at 50° C. for accelerating the desired equilibration. The flow rate is preferably set to about 1 ml per minute. This results in a transfer time of about 1 minute.

The equilibrated mixture of water and $CO_2$ flows through the line 15 into the degassing unit 12. A tubular, gas-permeable membrane of length 5-10 cm and internal diameter 1.8 mm is disposed there in a Plexiglas tube of the same length (internal diameter 4.5 mm). Both tubes 31, 32 are accommodated in an aluminum casing 33 for sealing against the surrounding air. The $CO_2$ contained in the mixture passes through the membrane into the Plexiglas tube 32 and is removed from there. To this end, a helium stream is conducted in parallel and in the same direction as (alternatively in the opposite direction to) the mixture of water and $CO_2$ in the degassing unit 12. The gas inlet 20 is fed from a helium source (not shown). A mixture of helium and $CO_2$ leaves the gas outlet 19.

The transfer of the $CO_2$ into the Plexiglas tube 32 is dependent upon the pressure differential within and outside the tube 31. This pressure differential is about half an atmosphere. In other words, the pressure in the helium carrier gas is about 0.5 bar less than in the water within the tube 31. The pressure is determined by the cross sections of the lines in question, by the output of the pump 27 and the setting of the back pressure regulator 22. The pressure of the $CO_2$ before entry into the water line 13 also has an influence.

The mixture of carrier gas and $CO_2$ is fed from the gas outlet 19 through a first drying unit 34, a changeover valve 35 and a second drying unit 36 to an open split 37. From there, the carrier gas together with $CO_2$ enters an isotope mass spectrometer (IRMS). Alternatively or additionally, helium may be fed or added in the open split, see feed 38. It is also possible to feed a reference gas.

The first drying unit 34 is designed as a water trap and freezes the water still remaining in the gas out. The cooling is effected by dry ice (−78° C.).

The second drying unit 36 is a NAFION tube having a helium counter stream. This drying principle is also known. The aim is to prevent any water content in the gas.

The valve 35 consists of two switching valves V2 and V3. In the arrangement shown in FIG. 1, the carrier gas together with $CO_2$ passes from the first drying unit 34 to the second drying unit 36. When V2 and V3 are switched, the carrier gas together with $CO_2$ is discharged, while exclusively carrier gas is fed to the second drying unit 36. This allows maintenance work to be carried out on the first drying unit 34 without interrupting the carrier gas stream into the mass spectrometer.

Parallel to pump 27 and line 28, a pump 39 with an intake line 40 and pressure line 41 is connected to the valve V1. Standard water can be fed to the apparatus via the intake line 40 as a comparative sample. In this manner, switching of the valve V1 allows rapid and simple switching between the sample to be analyzed and standard water. In FIG. 1, the valve V1 is switched for passing through the sample to be analyzed. The standard water is at the same time passed through the valve V1 into a waste stream 42.

In a simpler embodiment, the pressure line 28 is connected directly to the water line 13. The parts having the numbers 40, 39, 41 and 42 are then not provided.

Figure 3:
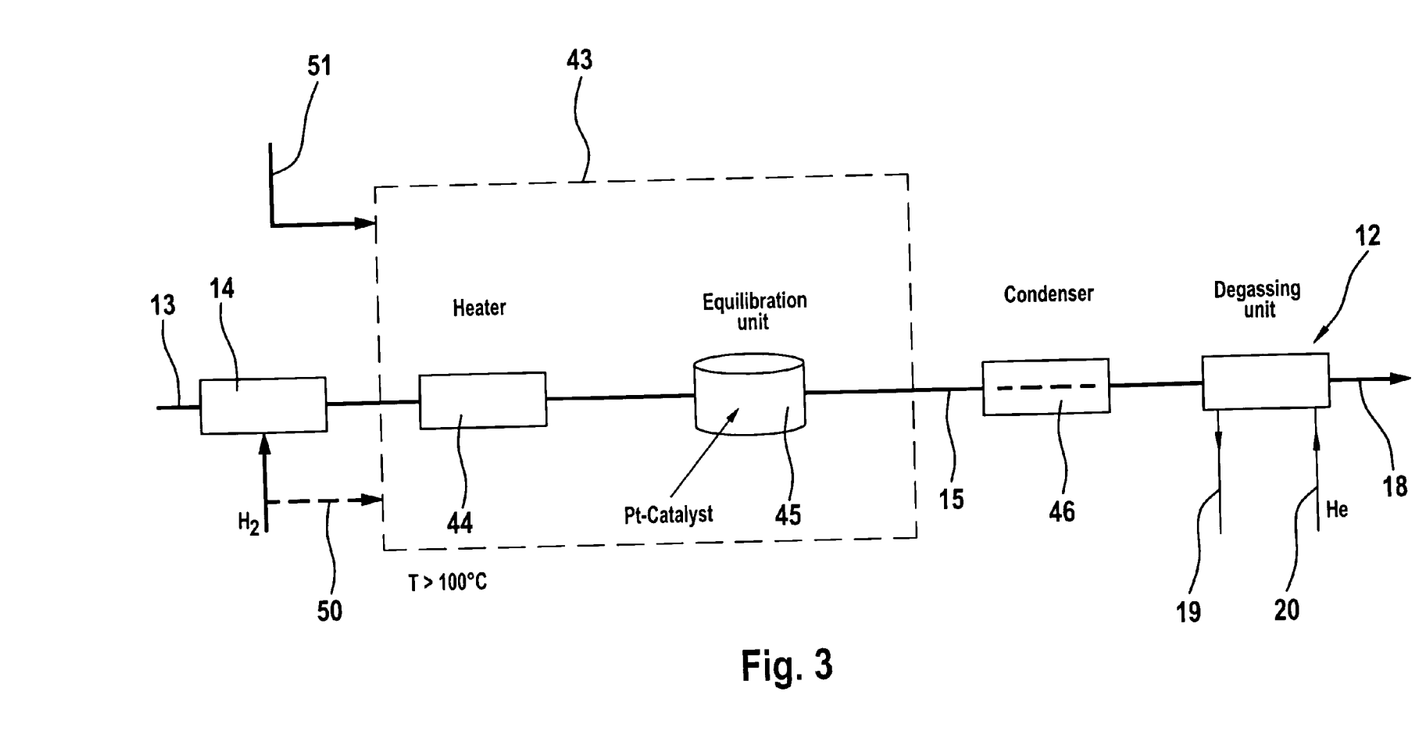
FIG. 3 shows a basic illustration of the apparatus for providing hydrogen for isotopic analysis.

According to FIG. 3, parts of the apparatus illustrated with the aid of FIGS. 1 and 2 are modified for the isotopic analysis of hydrogen. The gas inlet 14 is coupled to a hydrogen source. In addition to the thin tube, (similar to tube 30 in FIG. 1) which is not shown, an equilibration unit 43 has a stronger heater 44 which allows heating to above 100° C. (even evaporation). Also, a catalyst 45 is provided downstream of the heater 44, i.e. additionally thereto, which substantially accelerates the process of equilibration of the hydrogen from water with $H_2$. The mixture of water (especially steam) and hydrogen ($H_2$) leaving the equilibration unit 43 via line 15 contains a relatively large amount of water. The latter may be partially separated by an optionally provided condenser 46 upstream of the entrance into the degassing unit 12.

The degassing unit 12 may have exactly the same design as in the illustration of FIG. 2 and is only shown in simplified form in FIG. 3.

The equilibration unit 43 may also be a reaction chamber with a heater and be charged with a catalyst, in particular of platinum, uranium or zinc. The equilibration of the $H_2$ is extremely temperature-sensitive. The heater 44 and the catalyst 45 are therefore arranged in very close spatial proximity, in order to be able to carry out the equilibration at a precisely defined temperature.

As a result, the invention enables a rapid and precise feed of hydrogen and/or oxygen isotopes from a water sample or from an ice sample for isotopic ratio determination in a mass spectrometer provided therefor.

Figure 4:
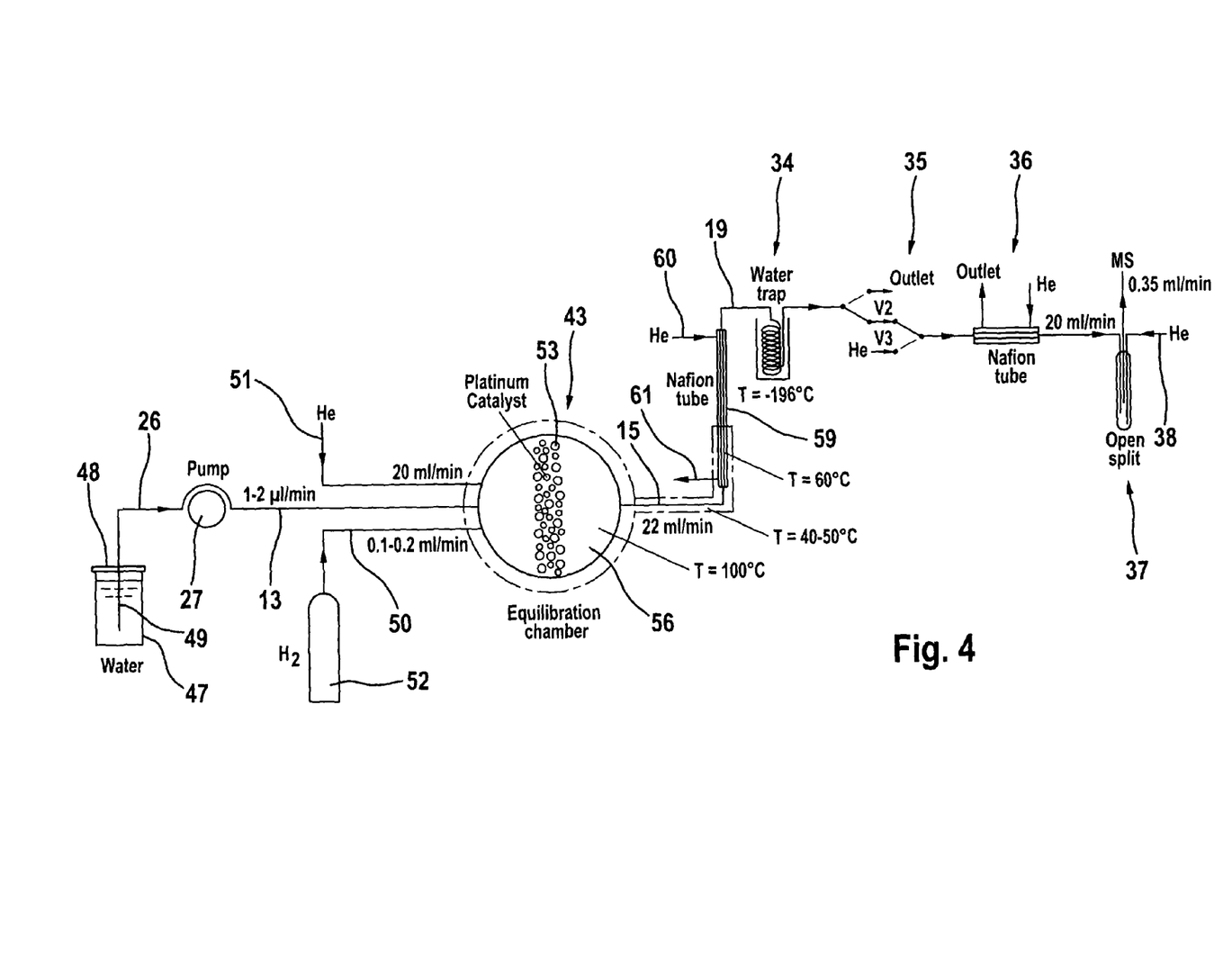
FIG. 4 shows an overview of the individual constituents of an apparatus according to the invention for providing hydrogen for isotopic analysis.
Figure 5A:
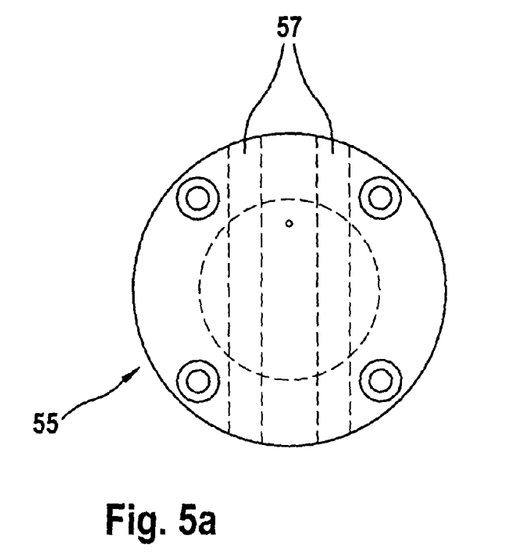
FIG. 5a is a plan view of a lid of the equilibration unit.
Figure 5B:
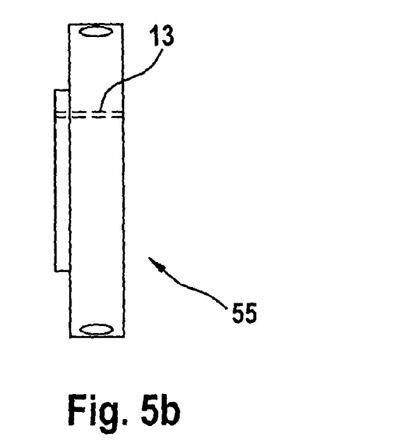
FIG. 5b is a side view of the lid of FIG. 5a, FIG. 5c is a plan view of a bottom of the equilibration unit.
Figure 5C:
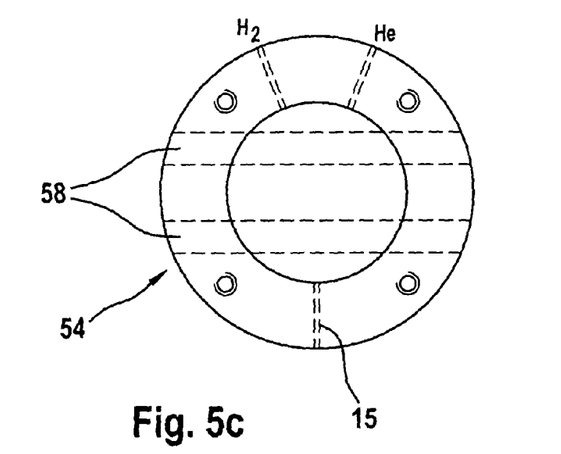
Figure 5D:
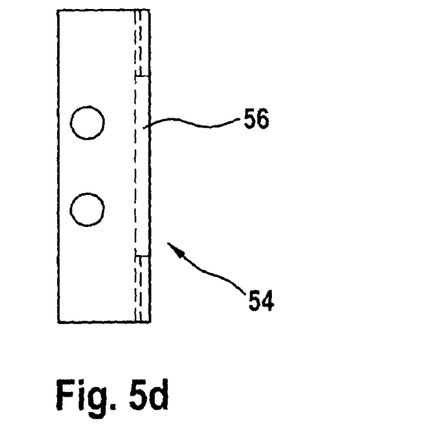
FIG. 5d is a side view of the bottom of FIG. 5c.

FIG. 4 relates to the isotopic analysis of the hydrogen contained in the water. Liquid water may be fed as illustrated in FIG. 1. Alternatively, FIG. 4 shows the provision of a water sample in a vessel 47, consisting in particular of glass, which is sealed in a vapor-tight manner by a rubber membrane 48. The vessel 47 and the rubber membrane 48 are pierced by a hollow needle 49, through which the water passes into the intake line 26. It is also possible to evaporate the water (not shown) before entry into the equilibration unit 43, or equally to feed a vaporous sample.

In this case, the equilibration unit 43 has a special design. As already illustrated with the aid of FIG. 3, heater and catalyst material are integrated. The equilibration unit 43 is a chamber with line 13 as the inlet, a separate hydrogen inlet 50, a carrier gas inlet 51 and line 15 as the outlet for a mixture of carrier gas, steam and hydrogen. For the feed into the equilibration unit 43, the hydrogen is taken from a hydrogen reservoir 52.

The catalyst charge 53 consists of platinum-coated catalyst spheres of approximately 1 millimeter diameter. The carrier gas provided is helium which flows into the equilibration unit 43 at 20 ml/min. In comparison, hydrogen is fed in a stream of 0.1 to 0.2 ml/min. The liquid water in line 13 flows at about 1 to 2 microliters/minute. A gaseous mixture leaves the equilibration unit 43 at a flow rate of about 22 ml/min.

The equilibration unit 43 is also referred to as a deuterium chamber and in the present case is designed in two sections with a bottom 54 and a lid 55 which form a cavity 56 of about 2 to 5 ml between them.

Bottom 54 and lid 55 each have two heating cartridges 57, 58 for heating and evaporating, so that there is a total heating output of about 400 watt.

The catalyst charge 53 (about 50 to 100 HOKO beads), or alternatively uranium or zinc, are arranged in a basket of fine stainless steel mesh in the middle of the cavity 56 (not shown).

Lid 55 and bottom 54 are held together by four screws and are sealed against each other by an indium wire (not shown).

Downstream of the equilibration unit 43, along line 15, is disposed a NAFION tube. NAFION refers to a special material which is gas-impermeable but water-permeable, especially to steam. The NAFION tube 59 serves in this case as a degassing or drying unit and removes the majority of the water from the mixture of carrier gas, hydrogen and steam. As is customary, a carrier gas counter stream is conducted in the NAFION tube 59, and there is a carrier gas inlet 60 an outlet 61 for the mixture of stream and carrier gas, in particular helium.

Downstream of the gas outlet 19 of the NAFION tube 59 are provided further apparatus parts in accordance with FIG. 1, such as a cold trap as a drying unit 34, the changeover valve 35, a NAFION tube as a further drying unit 36 and the open split 37. A degassing unit for separating liquid as in FIGS. 1 to 3 is not provided in this case.

In this case, the equilibration unit 43 and the cavity 56 are heated to 100° C. The water entering via line 13 immediately evaporates completely. When the hydrogen is fed continuously (inlet 50), an average residence time (exchange time) in the cavity 56 of about 6 seconds at a volume of 2 ml and about 15 seconds at a volume of 5 ml is achieved. Complete HD equilibration is the consequence.

The helium entering via inlet 51 continuously purges the cavity 56 and transports the mixture (helium, hydrogen, steam) into the NAFION tube 59. In this case, line 15 is heated to about 40-50° C. The NAFION tube 59 has a length of about 60 centimeters. The first quarter of it is heated to 60° C. This temperature is about 10 to 20° C. above the dew point of the gas. The helium counter stream in the NAFION tube 59 flows at about three times the rate of the entering gas stream (steam, hydrogen and helium) and is about 60 to 70 ml/min. Pressures and temperatures in this case are preferably selected in such a way that no condensate occurs in the region of the NAFION tube 59.

Downstream of the NAFION tube 59, steam still present is efficiently removed in the cold trap 34. The coolant is preferably liquid nitrogen at a temperature of −196° C.

One of the features of the implementation example of FIG. 4 is that the mixture of residual substance and reaction product is present exclusively in gaseous form and thus no degassing unit is used. Only steam is removed. It may also be contemplated to feed steam as the starting substance.

EXAMPLES

The following detailed examples are provided to demonstrate the present invention. The examples are provided herein for illustration purposes only and are in no way intended to limit the scope of the invention.

Figure 6:
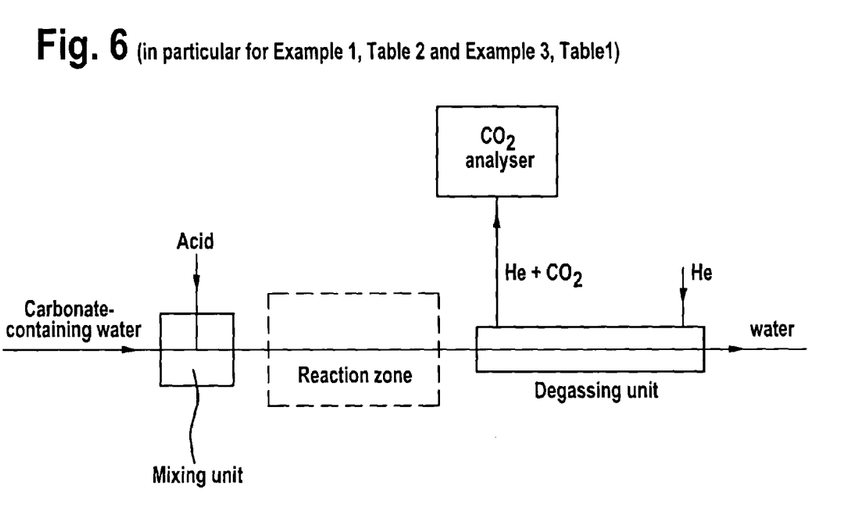
FIG. 6 is a schematic diagram of an apparatus according to the invention for providing $CO_2$ for the analysis of the carbonate content of a water sample.
Figure 7:
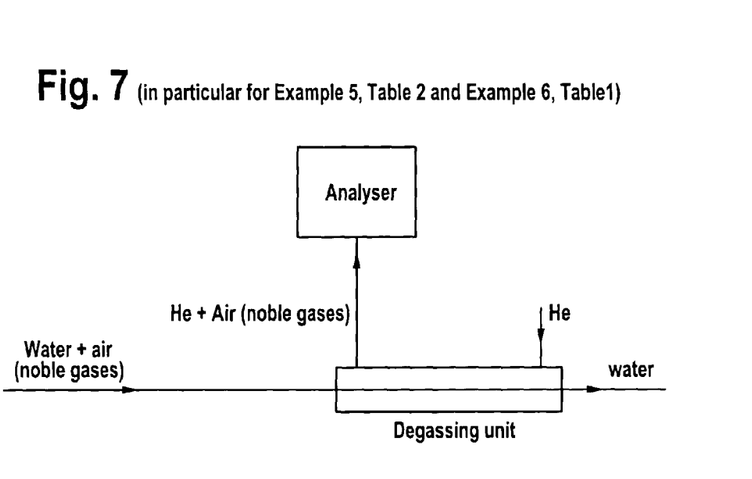
FIG. 7 is a schematic diagram of an apparatus according to the invention for providing air for the analysis of the air composition or of the isotopic composition of the air components.

In Table 1 and Table 2, a plurality of examples are in each case systematically listed for the application of the invention in the context of isotopic analyses (Table 1) and elemental analyses (Table 2). The diagrams of FIGS. 6 and 7 also refer thereto. FIG. 6 relates in particular to Example 1, Table 2 and Example 3, Table 1. FIG. 7 relates in particular to Example 5, Table 2 and Example 6, Table 1. Importance also attaches to the footnotes given under each of the tables.

Example No. 1 of Table 2 relates to the analysis of carbonate-containing water. The carbonate may be present as calcium carbonate, magnesium carbonate or potassium carbonate. The carbonate is present in ionic form, i.e. as carbonate $CO_3(2-)$, as bicarbonate $HCO_2(-)$ and also as $CO_2$. In neutral water (pH 7), the carbonate:bicarbonate:$CO_2$ ratio is 90:9:1. The water is continuously conducted by a water pump to a mixing unit in which it is continuously admixed with acid. This changes the pH and forces the equilibrium completely to the $CO_2$ side in the course of the reaction zone. In the downstream degassing unit, the $CO_2$ is separated from the water and conducted with a helium stream into a $CO_2$ analyzer. The $CO_2$ analysis results in a quantitative carbonate content determination, since the $CO_2$ content is proportional to the carbonate content.

When the $CO_2$ analyzer is replaced by a mass spectrometer, the carbon isotope content of the carbonate ($\delta^{13}C$) and also the oxygen isotope content of the water may be determined, see Table 1, Example 3.

The apparatus shown in FIG. 6 may also be used solely as a degassing unit, see FIG. 7. The apparatus may be used in this form as an isotopic or elemental analysis unit for ground water, ice water, etc., see in particular Table 2, Example 5 and Table 1, Example 6.

Example 1 in Table 1 relates to FIG. 1; the examples 2a, 2b in Table 1 relate to FIGS. 3 and 4.

In the Table 1 and Table 2, the starting substance is water or at least an aqueous solution. This also includes blood, urine, etc., and also all further medicinal or pharmaceutical areas of application.

Exemplary Embodiments

The following descriptions of exemplary embodiments of the invention are provided for illustration purposes. They are not intended to limit the scope of the invention in any way.

In a first (E1) embodiment of the present invention, a process is provided for generating a gaseous substance for the analysis of chemical elements or compounds. In this process, the elements or compounds are contained in a starting substance, the starting substance is continuously admixed with a reagent substance, at least one gaseous reaction product is formed which contains information about the elements or compounds of the starting substance and a residual substance, the gaseous reaction product is separated from the residual substance, and the reaction product is finally removed for an analysis.

In a second (E2) embodiment of the present invention, a process is provided as in embodiment E1 further characterized in that at least one of the elements H, O, C, S, P or N is contained in the starting substance.

In a third (E3) embodiment of the present invention, a process is provided as in embodiments E1 or E2, further characterized in that the residual substance is liquid on separation from the gaseous reaction product.

In a fourth (E4) embodiment of the present invention, a process is provided as in embodiment E3, further characterized in that the separation of the reaction product from the residual substance is carried out at a membrane which is gas-permeable and liquid-impermeable.

In a fifth (E5) embodiment of the present invention, a process is provided as in embodiment E4, further characterized in that the gaseous reaction product is entrained and removed by a carrier gas stream on a gas side of the membrane.

In a sixth (E6) embodiment of the present invention, a process is provided as in any of embodiment E1 to E5, further characterized in that the starting substance is a liquid.

In a seventh (E7) embodiment of the present invention, a process is provided as in embodiment E6, further characterized in that the starting substance is an aqueous liquid.

In an eighth (E8) embodiment of the present invention, a process is provided as in embodiment E6, further characterized in that ice is melted continuously to provide the liquid water or aqueous liquid.

In a ninth (E9) embodiment of the present invention, a process is provided as in any of embodiments E1 to E8, further characterized in that the reagent substance is a gas.

In a tenth (E10) embodiment of the present invention, a process is provided as in any of embodiments E1 to E9, further characterized in that at least one constituent of the reagent substance equilibrates with at least one of the elements of the starting substance or at least partially takes on its elemental or isotopic information.

In an eleventh (E11) embodiment of the present invention, a process is provided as in any of embodiments E1 to E10, further characterized in that at least one constituent of the reagent substance reacts with at least one constituent of the starting substance and thus forms the gaseous reaction product.

In an twelfth (E12) embodiment of the present invention, a process is provided as in any of embodiments E1 to E11, further characterized in that the reagent substance changes the pH of the starting substance, and in that this results in the gaseous reaction product being formed.

In an thirteenth (E13) embodiment of the present invention, a process is provided as in any of embodiments E1 to E12, further characterized in that the reaction product and the residual substance are present in gaseous form and are separated from one another in gaseous form.

In an fourteenth (E14) embodiment of the present invention, a process is provided as in embodiment E1, further characterized in that the starting substance is present in gaseous form and is admixed thus with the reagent substance.

In an fifteenth (E15) embodiment of the present invention, a process is provided as in embodiment E1, further characterized in that at least one of the substances starting substance, reagent substance, reaction product and residual substance is heated.

In a sixteenth (E16) embodiment of the present invention, a process is provided for generating a gaseous substance for the analysis of chemical elements or compounds. In this process, the elements or compounds are contained in a liquid starting substance as gases or as constituents of gases, the starting substance is passed through a degassing unit, in the degassing unit, the gases are separated from the liquid starting substance, after leaving the degassing unit, the gases are removed for analysis.

In an seventeenth (E17) embodiment of the present invention, a process is provided as in embodiment E16, further characterized in that the starting substance is liquid water or at least an aqueous solution.

In an eighteenth (E18) embodiment of the present invention, an apparatus is provided for the analysis of chemical elements or compounds. This apparatus comprises a reaction unit for the reaction of a starting substance containing the elements or compounds with a reagent substance, a means for continuously feeding the starting substance and the reagent substance into the reaction unit, and a separating unit further comprising means for separating a gaseous reaction product from a residual substance. The separating unit has a first outlet for the residual substance and a second outlet for the reaction product. Also provided are a means for passing the reaction product on from the separating unit to an analytical instrument.

In an nineteenth (E19) embodiment of the present invention, an apparatus is provided according to embodiment E18, further characterized in that the separating unit has a membrane which is gas-permeable and at the same time liquid-impermeable.

In an twentieth (E20) embodiment of the present invention, an apparatus is provided according to embodiment E18 or E19, further characterized by heating equipment for heating at least one of the substances starting substance, reagent substance, reaction product and residual substance.

In an twenty-first (E21) embodiment of the present invention, an apparatus is provided according to embodiment E18, further comprising a melt unit for melting solid starting substances.

In an twenty-second (E22) embodiment of the present invention, an apparatus is provided for generating a gaseous substance for the analysis of chemical elements or compounds. The apparatus comprises a degassing unit (12) having a liquid inlet, a liquid outlet and a gas outlet (19). In the degassing unit (12) is disposed a gas permeable and liquid impermeable membrane which separates a liquid zone from a gas zone. The gas zone is coupled to the gas outlet (19), and liquid inlet and liquid outlet are coupled to the liquid zone. From the gas outlet (19) there is a connection to an instrument for the analysis of the elements or compounds.

In an twenty-third (E23) embodiment of the present invention, an apparatus is provided according to embodiment E22, further characterized in that the degassing unit (12) has a gas inlet (20) coupled to the gas zone.

The foregoing description of specific embodiments and examples of the invention have been presented for the purpose of illustration and description, and although the invention has been illustrated by certain of the preceding examples, it is not to be construed as being limited thereby. They are not intended to be exhaustive or to limit the invention to the precise forms disclosed, and obviously many modifications, embodiments, and variations are possible in light of the above teaching. It is intended that the scope of the invention encompass the generic area as herein disclosed, and by the claims appended hereto and their equivalents.

TABLE 1

Examples of Isotopic Analyses

| Example No. | Starting substance gaseous/liquid | Elements of interest | Equilibration substance added gaseous/liquid | Equilibration gas to be removed | Residual liquid substance to be removed from the equilibration gas | Information |
|---|---|---|---|---|---|---|
| 1 | Water* Liquid | O | Gaseous $CO_2$ | $CO_2$ | Water | $\delta^{18}O$ of $H_2O$ |
| 2a+ | a) Water* liquid | a) H | a) Gaseous $H_2$ | a) $H_2$ | a) Water | $\delta D$ of $H_2O$ |
| 2b& | b) Water* liquid | b) H | b) Gaseous $H_2$ | b) $H_2$ | b) Steam | $\delta D$ of $H_2O$ |
| 2c° | B) Water* gaseous | b) H | b) Gaseous $H_2$ | b) $H_2$ | b) Steam | $\delta D$ of $H_2O$ |
| 3 | Carbonate-containing water* ($MgCO_3$ or $K_2CO_3$ or $CaCO_3$ + $HCO_3(-)$ + $CO_3(2-)$ + ...) | C | Acid (e.g. orthophosphoric acid $H_3O_4P$) | $CO_2$ formed by the reaction | Water containing $Mg(2+)$ $K(2+)$ $Ca(2+)$ | $\delta^{13}C$ of carbonate plus $\delta^{18}O$ of $H_2O$ |
| 4 | Sulfate-containing water* ($CaSO_4$ or $MgSO_4$ or $K_2SO_4$ etc.) | S | Acid (e.g. orthophosphoric acid $H_3O_4P$) | $SO_2$ formed by the reaction | Water containing $Ca(2+)$ $Mg(2+)$ $K(2+)$ | $\delta^{18}S$ of sulfur plus possibly $\delta^{18}O$ of $H_2O$ |
| 5 | Nitrate-containing water* ($NaNO_3$) | N | pH-dependent reaction | Nox (NO, $NO_2$, $N_2O$, $NH_3$) | Water | $\delta^{13}N$ |
| 6 | Ice, ground water* | All isotopes in air | none | Air components | Water | Isotopic composition of the air components |

+With reference to FIG. 3.
&: No degassing unit is used here, since only gaseous substances are present. However, these gaseous substances are conducted through a drying unit (NAFION tube) before analysis, see FIG. 4.
°: According to FIG. 4, when the samples have also been fed in gaseous form. For example, gaseous feed of water vapor in air.
In Examples 3-5, salts of the corresponding elements are usually dissolved in water (present as ions) and may partly be released as gas by changing the pH.
*: The term water also covers all aqueous solutions such as blood, urine, etc.

TABLE 2

Examples of Elemental Analyses

| Example No. | Starting substance gaseous/liquid | Elements of interest | Gaseous/liquid substance added gaseous/liquid | Reaction product to be removed | Residual liquid substance to be removed from the reaction product | Information |
|---|---|---|---|---|---|---|
| 1 | Carbonate-containing water* ($MgCO_3$ or $K_2CO_3$ or $CaCO_3$ + $HCO_3(-)$ + $CO_3(2-)$ + ...) | C, or sum of ($CO_3(2-)$, $HCO_3(-)$, $CO_2$) | Acid (e.g. orthophosphoric acid $H_3O_4P$) | $CO_2$ formed by the reaction | Water containing $Mg(2+)$ $K(2+)$ $Ca(2+)$ | Carbonate content |
| 2 | Sulfate-containing water* ($CaSO_4$ or $MgSO_4$ or $K_2SO_4$ etc.) | S | Acid (e.g. orthophosphoric acid $H_3O_4P$) | $SO_2$ formed by the reaction | Water | Sulfate content |
| 3 | Phosphide-containing water* ($Ca_3P_2$) | P | pH-dependent reaction | $PH_3$ formed by the reaction | Water containing $Ca(2+)$ $Mg(2+)$ $K(2+)$ | Phosphorus content |
| 4 | Nitride-containing water* ($NaNO_3$) | N | PH-dependent reaction | NOx (NO, $NO_2$, $N_2O$, $NH_3$) | Water | Nitrate content |
| 5 | Ice, ground water* | All elements in air | none | Air components | Water | Air composition |
| 6 | Water* | Rn# | None | Radon gas | Water | Radon content |

+With reference to FIG. 3
Radon as a radioactive noble gas, analytical instrument (α-detector)
*The term water also covers all aqueous solutions such as blood, urine, etc.

Reference Numeral List

- 10 Water feed unit
- 11 Equilibration column
- 12 Degassing unit
- 13 Water line
- 14 Gas inlet (bubble generator)
- 15 Line
- 36 Second drying unit (Nafion tube)
- 37 Open split
- 38 Helium feed
- 39 Pump (tubing pump)
- 40 Intake line
- 41 Pressure line
- 16 Melt unit
- 17 Cooling equipment
- 18 Water outlet
- 19 Gas outlet
- 20 Gas inlet
- 21 Pressure gauge
- 42 Waste stream
- 43 Equilibration unit
- 44 Heater
- 45 Catalyst
- 46 Condenser
- 47 Vessel -continued Reference Numeral List

| | |
|---|---|
| 22 Back pressure regulator | 48 Rubber membrane |
| 23 Waste stream | 49 Needle |
| 24 Ice rod | 50 Hydrogen inlet |
| 25 Melt head | 51 Carrier gas inlet |
| 26 Intake line | 52 Hydrogen reservoir |
| 27 Pump (tubing pump) | 53 Catalyst charge |
| 28 Pressure line | 54 Bottom |
| 29 $CO_2$ reservoir | 55 Lid |
| 30 Tube | 56 Cavity |
| 31 Tube | 57 Heating cartridges |
| 32 Plexiglas tube | 58 Heating cartridges |
| 33 Casing | 59 Nafion tube |
| 34 First drying unit (water trap) | 60 Inlet |
| 35 Changeover valve | 61 Outlet |

What is claimed is:

1. A continuous process for providing a gaseous substance for the isotopic or elemental analysis of chemical elements or compounds, comprising the steps of:
    a) providing a liquid starting substance containing the chemical elements or compounds;
    b) continuously mixing a stream of said liquid starting substance with a stream of a reagent substance, forming a mixture;
    c) continuously reacting at least one constituent of said liquid starting substance with at least one constituent of said reagent substance in said mixture resulting in the formation of at least one gaseous reaction product and a liquid residual substance, wherein said gaseous reaction product contains information about the chemical elements or compounds of said liquid starting substance;
    d) continuously separating said gaseous reaction product from said liquid residual substance thereby resulting in the formation of a stream of said liquid residual substance and a separate stream of said gaseous reaction product; and
    e) using the stream of said gaseous reaction product for said isotopic or elemental analysis of the chemical elements or compounds.

2. The process according to claim 1, wherein at least one of the elements H, O, C, S, P and N is contained in said starting substance, is present in the gaseous reaction product for said isotopic or elemental analysis, and is the chemical element for which the isotopic or chemical analysis is conducted.

3. The process according to claim 1 or claim 2, wherein said liquid residual substance is still a liquid after being separated from said gaseous reaction product.

4. The process according to claim 3, wherein said continuous separation of said gaseous reaction product from said liquid residual substance is carried out at a membrane, said membrane being gas-permeable and liquid-impermeable.

5. The process according to claim 4, wherein said gaseous reaction product is entrained and removed by a carrier gas stream on a gas side of said membrane.

6. The process according to claim 1, wherein said starting substance is an aqueous liquid.

7. The process according to claim 6, wherein ice is melted continuously to provide said liquid.

8. The process according to claim 1, wherein said reagent substance is a gas.

9. The process according to claim 1, wherein at least one constituent of said reagent substance equilibrates with at least one of the chemical elements of said starting substance.

10. The process according to claim 1, wherein the reagent substance changes the pH of the starting substance, and in that this change in pH results in the gaseous reaction product being formed.

11. The process according to claim 1, wherein at least one of said starting substance, said reagent substance, said reaction product, and said residual substance is heated.

12. The process according to claim 1, wherein said analysis is conducted with a mass spectrometer.

13. The process according to claim 1, wherein at least one constituent of said reagent substance at least partially takes on the elemental or isotopic information of said starting substance.

14. The process according to claim 1, wherein step d) is carried out at a temperature at which water is a liquid.

15. The process according to claim 1, wherein in steps c) or d) liquid water is present.

16. The process according to claim 1, wherein said starting substance is present in gaseous and liquid state during step c).

17. The process according to claim 1, wherein after step d) residual water is removed from the gaseous reaction product.

18. The process according to claim 17, wherein the water removal is done through a gas impermeable but water, including steam, permeable membrane.

19. A continuous process for providing a gaseous substance for the isotopic or elemental analysis of chemical elements or compounds, the process comprising the steps of:
    a) providing a liquid starting substance containing the chemical elements or compounds;
    b) continuously mixing a stream of said liquid starting substance with a stream of a reagent substance, forming a mixture, and continuously feeding the mixture of the starting substance and the reagent substance into a reaction unit;
    c) continuously reacting at least one constituent of said liquid starting substance with at least one constituent of said reagent substance in said mixture resulting in the formation of at least one gaseous reaction product and a liquid residual substance, and wherein said gaseous reaction product contains information about the chemical elements or compounds of said liquid starting substance;
    d) continuously separating said gaseous reaction product from said liquid residual substance thereby resulting in the formation of a stream of said liquid residual substance and a separate stream of said gaseous reaction product, wherein said liquid residual substance is still a liquid after being separated from said gaseous reaction product; and
    e) using the stream of said gaseous reaction product for said isotopic or elemental analysis of the chemical elements or compounds.

20. The process according to claim 19, wherein at least one of the elements H, O, C, S, P and N is contained in said starting substance, is present in the gaseous reaction product for said isotopic or elemental analysis, and is the chemical element for which the isotopic or chemical analysis is conducted.

21. The process according to claim 19, wherein said continuous separation of said gaseous reaction product from said liquid residual substance is carried out at a membrane, said membrane being gas-permeable and liquid-impermeable, and wherein said gaseous reaction product is entrained and removed by a carrier gas stream on a gas side of said membrane.

22. The process according to claim 19, wherein at least one constituent of said reagent substance equilibrates with at least one of the chemical elements of said liquid starting substance.

23. The process according to claim 19, wherein at least one of said liquid starting substance, said gaseous reagent substance, said reaction product, and said residual substance is heated.

24. The process according to claim 19, wherein step d) is carried out at a temperature at which water is a liquid.

25. The process according to claim 19, wherein in steps c) or d) liquid water is present.

26. The process according to claim 19, wherein said starting substance is present in gaseous and liquid state during step c).

27. The process according to claim 19, wherein after step d) residual water is removed from the gaseous reaction product.

28. The process according to claim 27, wherein the water removal is done through a gas impermeable but water, including steam, permeable membrane.

29. A continuous process for providing a gaseous substance for the isotopic or elemental analysis of chemical elements or compounds, comprising the steps of:
   a) providing a liquid starting substance containing the chemical elements or compounds;
   b) continuously mixing a stream of said liquid starting substance with a stream of a reagent substance, forming a mixture, and continuously feeding the mixture of the starting substance and the reagent substance into a reaction unit;
   c) continuously reacting at least one constituent of said liquid starting substance with at least one constituent of said reagent substance in said mixture resulting in the formation of at least one gaseous reaction product and a liquid residual substance, wherein the reagent substance changes the pH of the liquid starting substance, and in that this change in pH results in the gaseous reaction product being formed, and wherein said gaseous reaction product contains information about the chemical elements or compounds of said liquid starting substance;
   d) continuously separating said gaseous reaction product from said liquid residual substance thereby resulting in the formation of a stream of said liquid residual substance and a separate stream of said gaseous reaction product, wherein said liquid residual substance is still a liquid after being separated from said gaseous reaction product; and
   e) using the stream of said gaseous reaction product for said isotopic or elemental analysis of the chemical elements or compounds.

30. The process according to claim 29, wherein at least one of the elements H, O, C, S, P and N is contained in said starting substance, is present in the gaseous reaction product for said isotopic or elemental analysis, and is the chemical element for which the isotopic or chemical analysis is conducted.

31. The process according to claim 29, wherein said continuous separation of said gaseous reaction product from said liquid residual substance is carried out at a membrane, said membrane being gas-permeable and liquid-impermeable, and wherein said gaseous reaction product is entrained and removed by a carrier gas stream on a gas side of said membrane.

32. The process according to claim 29, wherein at least one constituent of said reagent substance equilibrates with at least one of the chemical elements of said liquid starting substance.

33. The process according to claim 29, wherein at least one of said liquid starting substance, said gaseous reagent substance, said reaction product, and said residual substance is heated.

34. The process according to claim 29, wherein the steps a), through d) are carried out at a temperature at which at least some of the water is a liquid.

35. The process according to claim 29, wherein step d) is carried out at a temperature at which water is a liquid.

36. The process according to claim 29, wherein in steps c) or d) liquid water is present.

37. The process according to claim 29, wherein said starting substance is present in gaseous and liquid state during step c).

38. The process according to claim 29, wherein after step d) residual water is removed from the gaseous reaction product.

39. The process according to claim 38, wherein the water removal is done through a gas impermeable but water, including steam, permeable membrane.

* * * * *